United States

Green

[11] 3,945,842

[45] Mar. 23, 1976

[54] CAST-FORMING COMPOSITION

[75] Inventor: Percy Green, Highland Park, N.J.

[73] Assignee: Johnson & Johnson, New Brunswick, N.J.

[22] Filed: Aug. 13, 1973

[21] Appl. No.: 387,867

[52] U.S. Cl............... 106/111; 106/15 R; 128/91 R
[51] Int. Cl.² ......................................... C04B 11/14
[58] Field of Search ............... 106/110, 111, 15 AF; 128/91

[56] References Cited
UNITED STATES PATENTS

| | | | |
|---|---|---|---|
| 2,251,610 | 8/1941 | Grande | 106/110 |
| 2,295,504 | 9/1942 | Shelton | 106/15 AF |
| 2,842,120 | 7/1958 | Foglia et al. | 128/91 R |
| 2,913,346 | 11/1959 | Hoffman | 106/111 |
| 3,746,680 | 7/1973 | Boricheski | 128/91 R |

OTHER PUBLICATIONS

"The Merck Index" 8th Ed., Merck & Co., Inc. Rahway N.J., 1968, pp. 126, 127 & 226.

*Primary Examiner*—Patrick P. Garvin
*Assistant Examiner*—John P. Sheehan
*Attorney, Agent, or Firm*—Steven P. Berman

[57] ABSTRACT

The invention provides a composition for forming casts which is a mixture of a settable cast-forming composition and a medically acceptable quaternary ammonium compound possessing bacteriostatic, wetting and accelerator properties.

6 Claims, No Drawings

CAST-FORMING COMPOSITION

This invention relates to settable compositions.

More particularly, this invention relates to the settable cast-forming compositions adapted for use as casts or e.g. orthopedic bandages, for immobilizing and/or supporting members or parts of the body.

Conventional cast-forming compositions for the above purpose are composed of a wettable, settable (hardenable) material, such as plaster of Paris and typically placed on a suitable substrate or backing such as a woven gauze fabric. The backing is normally in the form of an elongated strip or roll of material.

There are basically two types of settable compositions on backings in use today—the first and least used form being known in the art as a "loose plaster bandage", the second being a preformed "hard-coated" settable bandage. In the first type, the backing or substrate is dusted or otherwise coated with the settable material in a powder form and because of disadvantages in material drop-off in handling and use, this type has been replaced to a large extent by the second, preformed "hard-coated" type. In the preformed or "hard-coated" type, the settable material is precoated and dried so as to form a more or less integral composition with a substrate which is more readily acceptable for handling purposes as the settable composition does not tend to fall off. Normally, the settable composition of this type is coated on both sides of the substrate.

When using both of the above types of settable compositions, the product is dipped into an aqueous solution (normally water) which renders the settable composition moldable or flexible whereafter the product is wrapped or placed about a member of the body and permitted to harden or cure.

A still further method of using the settable compositions described above is without a backing, whereby the settable composition is rendered moldable by e.g. water and the composition then directly placed about the member or part of the body.

It has been conventional practice to incorporate into cast-forming settable compositions a wetting agent for the purpose of permitting rapid penetration of the water or similar fluid to render the composition moldable or flexible. Use of wetting agents reduces the amount of work and time required to render the compositions moldable or flexible and simplifies procedures involved in the application of the cast-forming composition while ensuring that they are substantially uniformly settable.

Typical of the wetting agents conventionally used for compositions rendered moldable or flexible by water, as in the case of plaster of Paris, are the sodium salts of alkylsulphosuccinates. Such wetting agents, to obtain the maximum benefit of their inclusion in the settable compositions, are generally present in quantities of from about 0.025 to 1% by weight.

However, the amount of wetting agent must be such that it does not render the settable composition "foamy", upon being wetted by, e.g. water, which would make the finished cast extremely weak and brittle. Normally, the compositions are used in a highly viscous form in which condition they are still moldable or flexible and yet are capable of conforming to the contours of the member to which they are applied.

Moreover, the amount of wetting agent is also limited to an amount below that which will cause "wash out"; a condition where e.g. the plaster of Paris upon being wetted for application to a locus of use, will come out of a backing or substrate to or on which it is applied (as in the case of preformed bandages), and not be available for use as part of the finished cast.

As is known in the art, settable compositions such as plaster of Paris ordinarily have no inherent inhibiting effect on the presence or reproduction of bacteria. The presence or growth of bacteria between the skin and the cast, and in the cast itself, may create problems. This problem is accentuated where casts are placed over wounds or points of irritation; hence, it has been suggested in the art that such cast-forming compositions be improved against bacterial growth or reproduction. To this end, various types of agents or compounds for this purpose have been proposed, a typical example being hexachlorophene.

In addition to wetting agents and bacteriostatic agents, conventional cast-forming compositions also include an accelerator as an additive, functioning for the purpose of decreasing the setting time for the compositions. Typical of accelerators conventionally used, generally in the form of finely ground powder, are calcium chloride, potassium sulphate, copper sulphate, etc. These accelerators are normally added in amounts of about 0.5% by weight of the cast-forming ingredients, where setting times of about 5 to about 8 minutes are desired; for faster setting times (termed extra fast setting in the art) e.g. about 2 to about 4 minutes, usually 3 times this amount of accelerator is added. The amount of accelerator employed is in a non-linear relationship to the setting time, and as will be seen from the above, shorter setting times require relatively large amounts of the accelerator compared to longer setting times, requiring smaller amounts.

The use of accelerator additives, while providing an advantageous feature, also impart undesirable properties to the cast-forming compositions. Thus, the amount of accelerator employed is critical as high amounts deleteriously affect the viscosity of the slurry used to coat the cast-forming compositions which in turn, adversely affect the processing of such compositions. Thus, e.g., the slurry tends to become too viscous so that it plugs the machinery used for applying the compositions onto the substrates. Moreover, above a given amount, no further apparent advantages are gained in adding increasing quantities of accelerator. Each separate agent, such as the wetting agent, and bacteriostatic agent, and accelerator agent, incorporated into the settable cast-forming compositions, represents an additional step involved in the production of such compositions and thus, adds to the cost of the resultant product, and generally interferes with the strength of the product. Thus, it would be desirable if, for such settable compositions, the function of certain of these agents could be combined thereby eliminating the necessity of incorporating separate agents for each function.

In accordance with this invention, it has unexpectedly been found that a selected group of compounds impart to settable cast-forming compositions, a combination of bacteriostatic properties and wetting properties, while simultaneously functioning as an accelerator, thereby eliminating additional steps in the manufacture of the composition, and the necessity of including separate components for these purposes, while at the same time imparting to the compositions additional desirable characteristics.

More particularly, with this invention, it has been unexpectedly found that medically acceptable quaternary ammonium compounds, when incorporated into settable cast-forming compositions, provide the composition with both bacteriostatic and wetting properties, while simultaneously functioning as an accelerator. The use of a quaternary ammonium compound in settable cast-forming compositions functioning as a combined bacteriostatic, wetting agent and accelerator was quite unexpected, since it was previously considered necessary to provide separate agents for each property to obtain maximum benefit for each agent in the composition; and further, it has not been suggested in the art that quaternary ammonium compounds would have the combined properties of acting as a bacteriostatic, wetting and accelerator agent.

Typical quaternary ammonium compounds functioning as a combined bacteriostatic, wetting and accelerator agent include benzalkoniumhalides, with the chloride being most preferred, as well as compounds such as cetyl-trimethyl-ammonium halides, e.g. the bromide, chloride and iodide thereof, with the bromide being particularly preferred.

The amount of the quaternary ammonium compound employed may be varied within wide ranges depending on the type of settable cast-forming composition employed. It has been found that at least about 0.025% (preferably 0.05 to 1.5%) by weight, of the quaternary ammonium compounds, based on the weight of the settable composition, is sufficient to obtain both bacteriostatic and wetting agent properties, and function as well as an accelerator.

The cast-forming ingredients or compositions useful with the present invention may be any suitable material conventionally employed for this purpose. Because of their availability and economical characteristics, most cast-forming settable compositions in use today are the water-wettable gypsum cements, and more particularly, what is known in the art as plaster of Paris - a gypsum cement. The plaster of Paris may be the ordinary variety as typically incorporated into cast-forming compositions, or may be of the high strength type referred to as alpha gypsum as disclosed in U.S. Pat. No. 1,901,051, issued Mar. 14, 1933 to Randel and Dailey. This strength gypsum is manufactured by calcination of gypsum rock in contact with steam at 17 to 20 lbs. gauge pressure, followed by drying and grinding. Alpha gypsum differs from ordinary plaster of Paris in that its compressive strength will range from 5000 lbs. per square inch on upward. Alpha gypsum is further differentiated from ordinary plaster of Paris or hemihydrate in the physical nature of individual crystal fragments composing the finely ground product.

As desired, the setting time for the cast-forming compositions of the present invention may be decreased, as in the case of extra fast setting compositions, by incorporating a minor amount of a conventional accelerator, such as those described above. In this respect, it has been found that the quaternary ammonium compound has a synergistic effect on the conventional accelerator agents whereby decreased setting times may be obtained by employing conventional accelerator agents with the quaternary ammonium compounds. Thus, if it is desired to decrease the setting time as for extra fast setting compositions, such conventional agents as employed for this purpose can be incorporated into the composition of the present invention in amounts less than those which were previously used for this purpose.

In greater detail, depending on the setting time desired, a conventional accelerator may be included in amounts ranging from about 5 to about 50% less than previously employed for this purpose. Thus, by adding a minute amount of the quaternary ammonium compounds, it is possible to replace a conventional large amount of an accelerator agent.

The unexpected synergistic action by the compositions of the present invention having the quaternary ammonium compounds, and an added conventional accelerator for the purpose of still further decreasing the setting time as for extra fast setting compositions, is unexpected since, as previously mentioned, separate agents were employed for this purpose and the amount of accelerator was not in a linear relationship to the setting time but rather, requires several times that amount of conventional setting agent for extra fast setting as compared to slower setting times with smaller amounts.

Various conventional additives may be included in the settable cast-forming compositions of the present invention, such additives being strengthening agents such as uncured aldehyde-triazine resins. Such strengthening agents may be included in amounts of from about 5 to about 30% by weight of the cast-forming composition, and impart greater cast strength and resistance to water after setting. Such aldehyde-triazine resins are well known in the art and are commercially available, and are described in U.S. Pat. No. 2,260,239 issued Oct. 21, 1941 to Talbott and 2,310,004 issued Feb. 2, 1943 to Widmer et al. Other additives which may be incorporated include binders which serve the purpose of effecting maximum adhesion of the plaster of Paris and resin to the bandage backing material. Suitable binders are polyvinyl acetate emulsions, described in U.S. Pat. No. 2,655,148. Other usable binders include emulsions or solutions of polymers of vinyl chloride, vinyl acetate, acrylates, methacrylates, or butadiene, or copolymers, interpolymers or polymeric mixtures thereof.

Additionally, the cast-forming settable compositions may also contain conventional amounts of plasticizers or "creaming" agents such as glycerols, glycols, polyglycols, natural and synthetic gums, etc. Retarders may also be included such as soluble citrates, phosphates, acetates, or other organic retarders. The above additives, when used are generally incorporated into the cast-forming composition when prepared, typically by blending the appropriate amount of additives therein.

The cast-forming settable compositions of the present invention having the combined bacteriostatic, wetting and accelerator agent component may be employed, after wetting, by the direct application to the locus of use without any backing or substrate, and permitted to set or harden. Alternately, and, according to present preferred practices, the composition of the present invention may be applied or included on a substrate or backing. As explained previously, such compositions are either in the form of a "loose powder package" or more recently, in a preformed "hard-coated" product form. The loose plaster packages may be prepared according to conventional procedures, for example, dusting or otherwise coating the composition onto the backing or substrate. In the case of preformed compositions, the settable composition may be formed into a paste or slurry, and impregnated on one or both surfaces of the substrate or backing, and permitted to dry. In either case, the products are then wetted by, for example, dipping them in water and once in a moldable condition, wrapped about the locus of use. When preparing preformed "hard-coated" products having the settable composition of the present invention, the steps of impregnating the composition onto the substrate or backing followed by drying are well known by those skilled in the art and may be carried out accordingly.

The substrate or backing used in the loose and preformed type of products may be any suitable substrate as, for example, woven and nonwoven fabrics, again according to conventional practices known to those skilled in the art. Such backings are normally of a relatively narrow width in comparison to the length thereof and usually a continuous length is wrapped about the body point or member to encase it several times to provide a cast of sufficient strength characteristics.

It has been found that the products of the present invention require less preparation time and as well, have an efficiency substantially the same as, if not better, than conventional compositions. Thus, for example, the settable composition will not normally contain the same amount of additives as would otherwise be included if separate agents were used for each purpose.

Having thus generally described the invention, reference will now be made to the accompanying Examples illustrating preferred embodiments.

EXAMPLE I

A conventional plaster of Paris formulation was prepared, minus wetting agents and accelerator, and to it was added 0.1% of benzalkonium chloride based on the weight of the plaster of Paris.

The formulation was coated on a woven backing, the product then being permitted to dry to form an orthopedic bandage.

Upon being dipped in water to render the plaster of Paris composition moldable for purposes of application of the bandage to a body member, it was found that the benzalkonium chloride provided very rapid wetting properties, comparable to a similar composition with a conventional additive for this purpose. It was also found in subsequent testing that there was inhibition of the growth of bacteria and that the properties of the cast made with the orthopedic bandage showed no deterioration.

EXAMPLE II

The procedures of Example I were repeated except that the plaster of Paris used contained a conventional wetting agent. To the composition there was added 0.1% by weight of the plaster of Paris benzalkonium chloride. The composition was then placed on a backing to form an orthopedic bandage. Upon dipping the bandage in water for application to a locus of use, it was found that the wetting properties imparted to the plaster of Paris mixture were quite excessive and caused a large amount of plaster to separate from the backing, in addition to the plaster of Paris-water mixture being foamy.

This Example demonstrates that the benzalkonium chloride functioning as a bacteriostatic agent on one hand, eliminates the requirement for a wetting agent since the benzalkonium chloride also imparted to the plaster of Paris the required wetting characteristics.

EXAMPLE III

A composition substantially identical to that of Example I was prepared, except in this case, the quaternary ammonium compound was cetyl-trimethyl-ammonium bromide. Similar results to those noted in Example I were obtained.

EXAMPLE IV

A composition was prepared by mixing together the following ingredients in the following amounts (including the conventional binding agents, etc.):
2600 grams Plaster of Paris
14.0 grams $K_2SO_4$
The setting time for the above composition was determined to be approximately 7–7.5 minutes.

EXAMPLE V

A composition identical to that of Example IV was prepared, except there was incorporated therein 1.5 grams of cetyl-trimethyl-ammonium-bromide. This composition was unexpectedly found to have a setting time of approximately 4 minutes, making it an "extra-fast setting" composition. In this case, the quaternary ammonium compound not only functioned to provide bacteriostatic and wetting agent properties to the composition, but in combination with an amount of conventional accelerator normally employed for compositions of an average setting time, there was obtained an extra-fast setting composition, thereby illustrating the apparently synergistic effect of the quaternary ammonium compound in combination with conventional accelerators.

EXAMPLE VI

A composition substantially identical to that of Example V was prepared, but in place of the ammonium bromide compound, there was employed 1.5 grams of benzalkonium chloride. Substantially, identical results were obtained with this composition as that outlined in Example V.

EXAMPLE VII

A composition similar to that of Example V was prepared, except that in this case, 32 grams of $K_2SO_4$ was included. The composition was found to possess the required wetting properties, and as well possess bacteriostatic properties. The inclusion of the conventional accelerator combined with the quaternary ammonium compound provided an extra-fast setting composition, which set in approximately 2.5–3 minutes. The composition also had the desirable attributes as described in Example IV.

What is claimed is:

1. In a composition for forming orthopedic casts and comprising a settable, water-wettable gypsum cement cast-forming composition, the improvement wherein said composition comprises a quarternary ammonium compound having bacteriostatic, wetting and accelerator properties, said quarternary ammonium compound selected from the group consisting of benzalkonium halides and cetyl-trimethyl-ammonium halides and being present in an amount of at least about 0.025% by weight based on the weight of the settable composition and less than that which would cause foaming.

2. The composition of claim 1 wherein said quarternary ammonium compound is present in an amount of about 0.025% to about 1.50% by weight based on the weight of the settable cast-forming composition.

3. In a composition for forming orthopedic casts and comprising a settable, water-wettable gypsum cement cast-forming composition, the improvement wherein said composition comprises a quarternary ammonium compound having bacteriostatic, wetting and accelerator properties, said compound being present in an amount of about 0.025% to about 1.5% by weight based on the weight of the settable composition and said compound selected from the group consisting of benzalkonium halides and cetyl-trimethyl-ammonium halides.

4. In an orthopedic bandage comprising a woven or nonwoven fabric having applied thereto a settable, water-wettable gypsum cement cast-forming composition, the improvement wherein said composition comprises a quarternary ammonium compound having bacteriostatic, wetting and accelerator properties, said quarternary ammonium compound selected from the group consisting of benzalkonium halides and cetyl-trimethyl-ammonium halides and being present in an amount of at least about 0.025% by weight based on the weight of the settable composition and less than that which would cause foaming.

5. The bandage of claim 4 wherein said quarternary ammonium compound is present in an amount of about 0.025% to about 1.50% by weight based on the weight of the settable cast-forming composition.

6. In an orthopedic bandage comprising a woven or a nonwoven fabric having applied thereto a settable, water wettable gypsum cement cast-forming composition, the improvement wherein said composition comprises a quarternary ammonium compound having bacteriostatic, wetting and accelerator properties, said compound being present in an amount of about 0.025% to about 1.5% by weight based on the weight of the settable composition and said compound selected from the group consisting of benzalkonium halides and cetyl-trimethyl-ammonium halides.

* * * * *